United States Patent [19]

Nedwick et al.

[11] Patent Number: 5,453,548
[45] Date of Patent: Sep. 26, 1995

[54] PURIFICATION OF DITERTIARY BUTYL PEROXIDE

[75] Inventors: Robert Nedwick, Broomall; Jeffrey M. McFarland, Brookhaven; Leonard A. Fabiano, Wayne, all of Pa.

[73] Assignee: ARCO Chemical Technology, L.P., Greenville, Del.

[21] Appl. No.: 328,638

[22] Filed: Oct. 25, 1994

[51] Int. Cl.$^6$ .................. C07C 409/16; C07C 409/00
[52] U.S. Cl. .................. 568/576; 568/558; 568/562; 568/569; 568/571; 568/577; 568/578
[58] Field of Search .................. 568/569, 576, 568/577, 558, 562, 578, 571

[56] References Cited

U.S. PATENT DOCUMENTS

| | | |
|---|---|---|
| 2,845,461 | 7/1958 | Winkler et al. .................. 568/569 |
| 3,864,216 | 2/1975 | Worrell et al. .................. 568/576 |
| 4,198,528 | 4/1980 | Kelsey .................. 568/578 |
| 4,381,222 | 4/1983 | Brossmann et al. .................. 568/576 |
| 4,900,850 | 2/1990 | Sanderson et al. .................. 568/578 |
| 5,149,885 | 9/1992 | Jubin, Jr. .................. 568/571 |
| 5,283,370 | 2/1994 | Hilderbrand et al. .................. 568/576 |
| 5,288,919 | 2/1994 | Faraj .................. 568/578 |
| 5,312,998 | 5/1994 | Liotta, Jr. et al. .................. 568/578 |

*Primary Examiner*—Werren B. Lone
*Attorney, Agent, or Firm*—William C. Long

[57] ABSTRACT

A process for the separation of ditertiary butyl peroxide form tertiary butanol is provided which includes the step of dehydrating the tertiary butanol to isobutylene and water.

5 Claims, 2 Drawing Sheets

PURIFICATION OF DITERTIARY BUTYL PEROXIDE

BACKGROUND OF THE INVENTION

Field of the Invention

The present invention relates to the separation of tertiary butyl alcohol (TBA) from ditertiary butyl peroxide (DTBP) by procedures which involve conversion of the TBA to isobutylene and water. In especially preferred practice, the invention relates to the separation of cetane additive quality DTBP from mixtures comprised of TBA, DTBP and also containing hydroperoxide impurities.

Prior Art

Tertiary butyl hydroperoxide (TBHP) is an important chemical of commerce which is generally produced by the molecular oxygen oxidation of isobutane as taught, for example, in U.S. Pat. Nos. 2,845,461 and 5,149,885.

Generally, tertiary butanol is produced in substantial amounts along with the tertiary butyl hydroperoxide during isobutane oxidation. Typically, isobutane oxidate contains 40–45 wt % TBHP and 55–60 wt % TBA. Methods are known for the production of ditertiary butyl peroxide by the catalytic reaction of tertiary butyl hydroperoxide with tertiary butanol and/or isobutylene. See for example, U.S. Pat. Nos. 5,312,998 and 5,288,919 as well as copending applications Ser. No. 08/102,017 filed Aug. 4, 1993 and allowed copending application Ser. No. 08/171,957 filed Dec. 22, 1993.

Generally, the production of ditertiary butyl peroxide by reaction of isobutylene with tertiary butyl hydroperoxide is preferred and indeed where mixtures of tertiary butanol and isobutylene are contacted with tertiary butyl hydroperoxide at reaction conditions, the predominant reaction is between isobutylene and tertiary butyl hydroperoxide and the resulting product is a mixture comprised of tertiary butanol and ditertiary butyl peroxide along with residual TBHP and small amounts of other by-product hydroperoxides and peroxides which are either present in isobutane oxidate or are made during the reaction. Included among such materials are secondary butyl t-butyl peroxide, diisobutylene t-butyl peroxide and the like.

In many applications, e.g. as a diesel fuel cetane improver, the ditertiary butyl peroxide must be substantially free of tertiary butanol and peroxidic impurities and therefore it becomes important to efficiently separate the ditertiary butyl peroxide and tertiary butanol and to obtain a ditertiary butyl peroxide product which is substantially free of tertiary butanol as well as peroxidic impurities.

Numerous studies have addressed the effect of diesel fuel cetane number on heavy-duty diesel engine emissions. The universal conclusion is that cetane additives, which are used to improve diesel fuel ignition quality, reduce the particulate matter, oxides of nitrogen, carbon monoxide, and hydrocarbon emissions. In addition, it is well established that cetane additives provide lower-cost cetane number increase than does the refinery option which involves increasing the natural cetane number through hydrogenation to reduce diesel fuel aromatic content. As the trend toward cleaner burning diesel fuels is growing worldwide, the use of higher cetane fuels is becoming a preferred option for meeting more stringent emission regulations.

Historically, nitrate esters, such as ethylhexyl nitrate, have been used commercially as cetane improvement additives. A review of both the open and patent literature finds numerous references using peroxide based cetane improvement additives. With some of these references dating back to the 1940's, the use of peroxide-based cetane improvement additives in and of itself is not new. Generally, the issues, which prevented commercial acceptance of peroxide-based cetane additives, included manufacturing cost, incompatibility with diesel fuel due to the presence of hydroperoxides, and the low flash point of diesel fuel resulting from the presence of TBA and other light materials which are present in the DTBP used to enhance the diesel fuel cetane number.

The thermal stability of the peroxide additive is one key to determining its compatibility with commercial diesel fuels. Unconverted TBHP and other residue hydroperoxides very easily form free-radicals upon thermal exposure during pre-combustion in the fuel delivery system. These free-radicals also oxidize and destroy diesel fuel lubricity. They must be removed from the DTBP cetane additive in order to provide a commercially acceptable product.

The other key issue is the presence of TBA and other low boiling materials present in the cetane additive. Upon blending of the DTBP cetane additive with diesel fuel, TBA, even present in low levels, will reduce the diesel fuel flash point below pipeline specifications. Thus, the DTBP must be substantially free of TBA and therefore it becomes important to efficiently separate the DTBP and TBA and to obtain a DTBP cetane additive which is substantially free to TBA. Separation by simple distillation is not feasible since TBA and DTBP form a low boiling azeotrope comprised of about 50 wt % of each component.

Recently, it has been established that "cetane additive" quality DTBP, when utilized to increase diesel fuel cetane number, lowers $NO_x$ emission to a greater extent than does the commercially available ethylhexyl nitrate cetane improver (see SAE Publication SP-994 "Diesel Fuel for the Nineties", page 155, Oct. 1993). This will be a significant advantage to the refiner and engine manufacture who are both in the process of developing new diesel fuel and engine technology which can meet the 1998 Clean Air Act target for $NO_x$ reduction from 5.0 to 4.0 grams/Brake Horse Power-Hour. The present invention provides a novel method and integrated process which gives cetane quality DTBP by efficient separation of DTBP substantially free of hydroperoxides and TBA.

The present invention provides a novel method for efficient separation of ditertiary butyl peroxide substantially free of tertiary butanol from mixtures of ditertiary butyl peroxide and tertiary butanol. In addition, during the separation process hydroperoxide contaminants are decomposed so that the recovered DTBP is substantially TBA and hydroperoxide free.

BRIEF DESCRIPTION OF THE INVENTION

In accordance with the present invention, separation of ditertiary butyl peroxide and tertiary butanol as well as decomposition of any contained hydroperoxide is accomplished by conversion of tertiary butanol in the presence of the ditertiary butyl peroxide to isobutylene and water by a dehydration reaction. The isobutylene and water can readily be separated from the ditertiary butyl peroxide by conventional phase separation and distillation procedures. An outstanding advantage of the invention is that tertiary butyl hydroperoxide and other hydroperoxide impurities present in the tertiary butanol and ditertiary butyl peroxide mixture are decomposed during the tertiary butanol dehydration and are thus effectively removed from the ditertiary butyl peroxide. In addition, isobutylene formed during the dehydration can be recycled to the ditertiary butyl peroxide forming step. The recovered DTBP is substantially free of TBA and hydroperoxides and is of diesel fuel additive quality.

DETAILED DESCRIPTION

Mixtures which are separated by the process of the invention are those comprised of ditertiary butyl peroxide and tertiary butanol such as result from the reaction of tertiary butyl hydroperoxide with isobutylene and/or tertiary butanol. Generally, such mixtures comprise by weight 30 to 60% ditertiary butyl peroxide, 25 to 55% tertiary butanol, 3 to 20% isobutylene, 0.5 to 5% tertiary butyl hydroperoxide, and 2 to 15% other materials.

Figure 1:
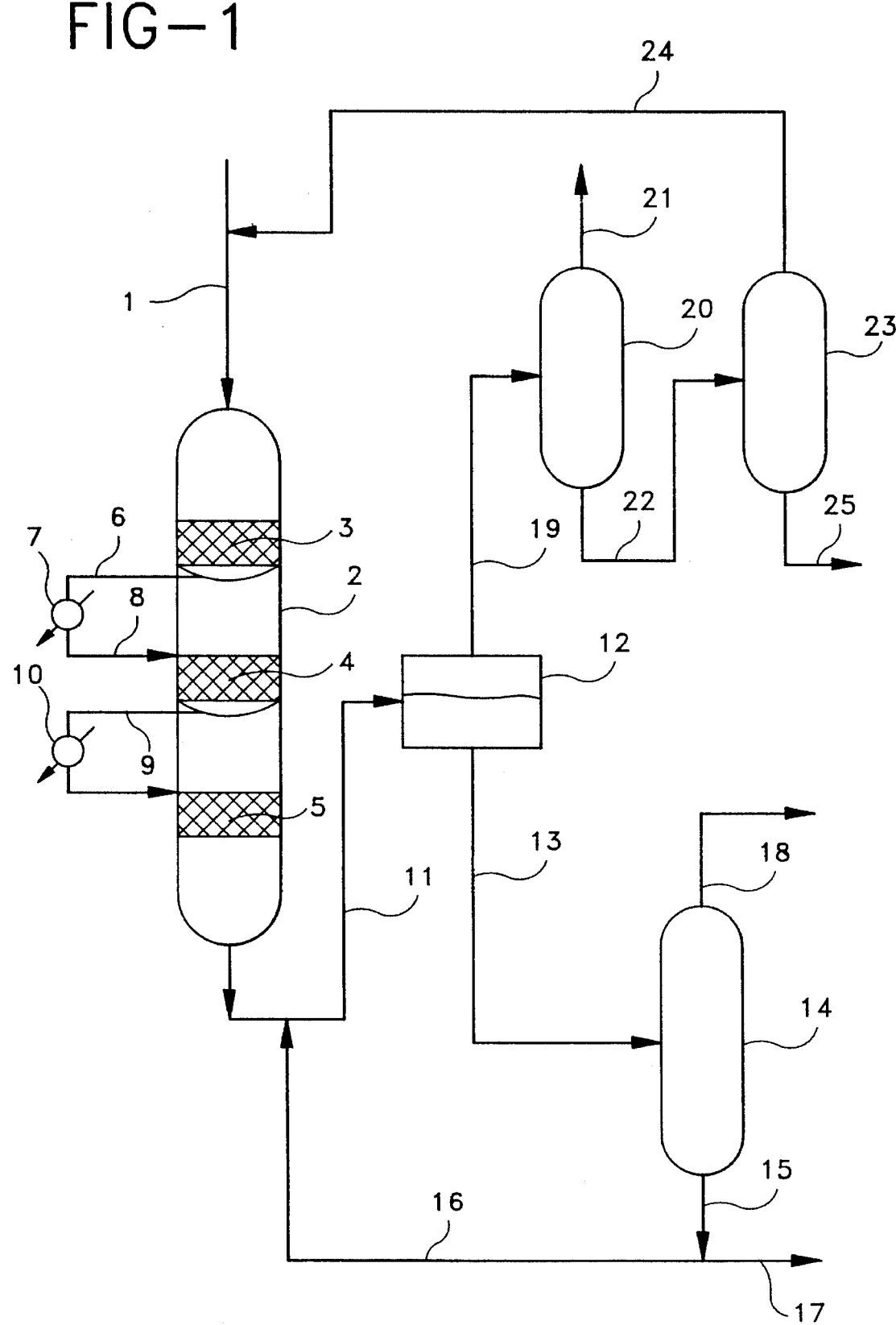
FIGS. 1 and 2 illustrate in schematic form embodiments of the invention.

Referring to the embodiment shown in attached FIG. 1, the mixture comprised of ditertiary butyl peroxide and tertiary butanol is fed via line 1 to dehydrator 2 wherein the tertiary butanol is dehydrated. Because the dehydration reaction is endothermic, it is advantageous to provide separate dehydration stages with interstage reheat as illustrated. Other dehydration apparatus can be used such as separate dehydration reactors and the number of stages or separate reactors can vary.

Zones 3, 4 and 5 in dehydrator 2 contain solid dehydration catalyst such as H—Y zeolite or another known solid dehydration catalyst appropriately supported in the dehydrator. The feed is heated to dehydration temperature (not shown) illustratively 80°–150° C., preferably 100°–130° C. prior to introduction into dehydrator 2. Upon passing through packed bed 3, tertiary butanol undergoes dehydration to isobutylene and water while the ditertiary butyl peroxide is largely unaffected. The reaction mixture from packed bed 3 is passed via line 6 to heater 7 wherein the mixture is heated to effective dehydration temperature and passed via line 8 to packed bed 4 for further dehydration. The dehydration reaction mixture is withdrawn from packed bed 4 via line 9 and passed to heater 10 wherein it is again heated to dehydration temperature and passed via line 11 to packed bed 5.

Upon passing through packed bed 5, the mixture is removed from dehydrator 2 via line 11 and passed to phase separator 12, optionally along with an aqueous recycle steam via line 16, wherein aqueous and organic phases are separated. Conditions in dehydrator 2 are maintained such that about 25–60% of the tertiary butanol fed is dehydrated therein. In addition, essentially all tertiary butyl hydroperoxide and other hydroperoxides in the feed are decomposed with the in situ formation of ditertiary butyl peroxide or tertiary butanol which in turn is substantially dehydrated.

The aqueous phase from separator 12 comprises tertiary butanol and water and other light materials such as acetone and passes via line 13 to distillation tower 14 for tertiary butanol recovery. In tower 14, the mixture is fractionally distilled and a waste water bottoms stream is removed via line 15 part of which is recycled via lines 16 and 11 to phase separator 12 to enhance tertiary butanol and ditertiary butyl peroxide separation with the remainder discarded via line 17.

A tertiary butanol and water azeotrope is taken overhead from tower 14 via line 18 for further processing and recovery of the tertiary butanol.

An organic phase comprised of ditertiary butyl peroxide, isobutylene and tertiary butanol is removed from phase separator 12 via line 19 and passes to column 20 wherein isobutylene is separated overhead via line 21 and this can conveniently be recycled to ditertiary butyl peroxide formation (not shown).

A bottoms stream of ditertiary butyl peroxide, tertiary butanol and other minor components passes from column 20 via line 22 to distillation column 23. A low boiling azeotrope of about 50 wt % tertiary butanol and 50 wt % ditertiary butyl peroxide is removed via line 24 and recycled to dehydrator 2.

Product ditertiary butyl peroxide essentially free of tertiary butanol (e.g. less than 1 wt %) and hydroperoxide (e.g. less than 0.1 wt %) is recovered via line 25.

In the embodiment described above, the dehydration conversion of tertiary butanol is limited to the equilibrium conversion of 25–60%. In an alternative embodiment described in FIG. 2, the conversion is not similarly limited.

Figure 2:
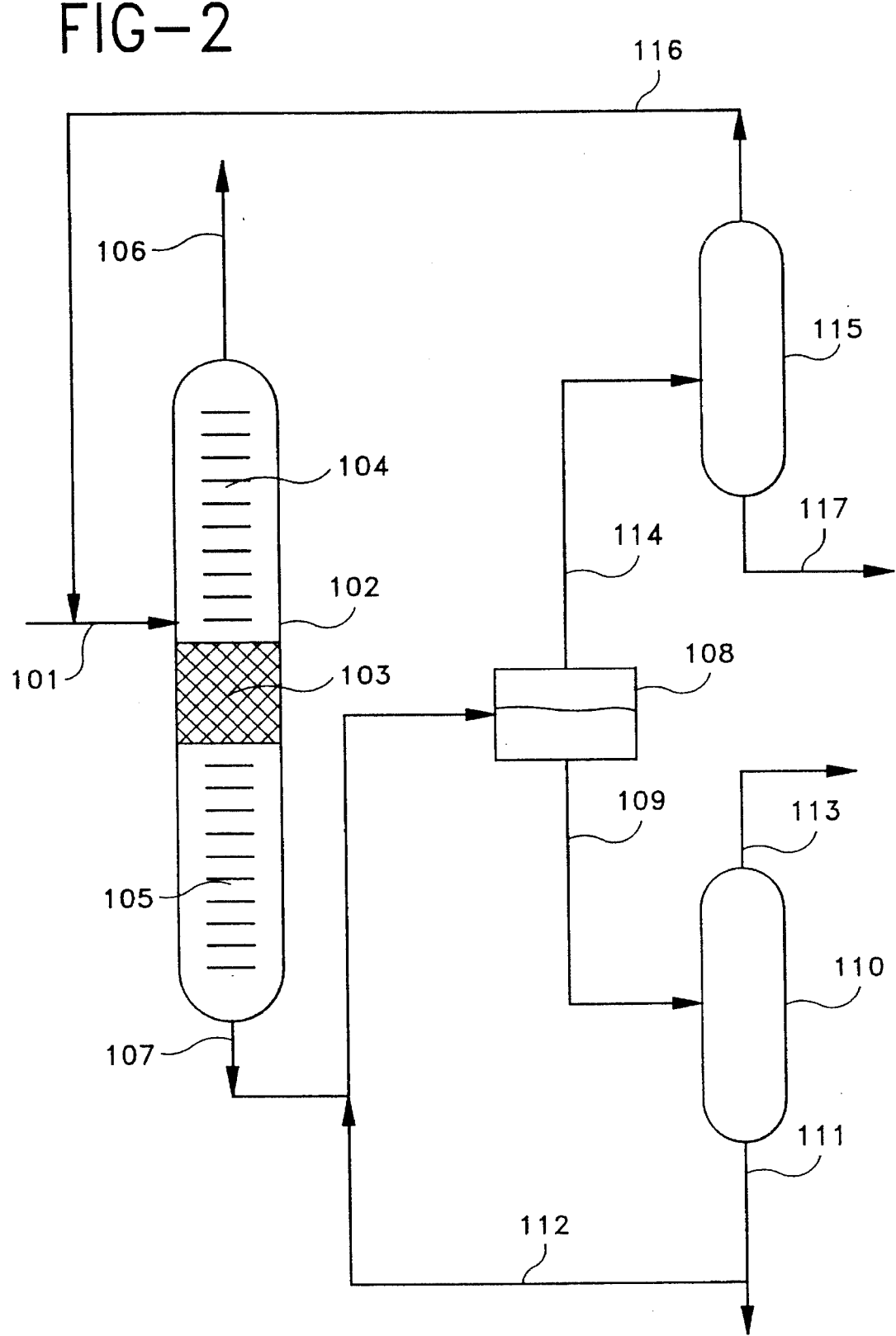

Referring to FIG. 2, the tertiary butanol dehydration is carried out in a reactive distillation column wherein isobutylene is removed as it is formed and thus the reaction is not equilibrium limited. The mixture comprised of ditertiary butyl peroxide and tertiary butanol is fed via line 101 to reactive distillation column 102 at an intermediate point. Column 102 is provided with a central packed catalyst bed 103 with fractional distillation zones 104 and 105 located respectively above and below the catalyst bed.

The feed tertiary butanol is dehydrated upon contact with the packed bed of catalyst and any tertiary butyl hydroperoxide or other hydroperoxide present is decomposed. The isobutylene product of dehydration passes upwardly through distillation zone 104 and is recovered via line 106. The recovered isobutylene is conveniently recycled to ditertiary butyl peroxide formation (not shown) with any excess recovered as a valuable co-product.

Ditertiary butyl peroxide, water and some tertiary butanol pass downwardly through distillation zone 105 and are removed via line 107 and passed to phase separation zone 108 optionally together with additional water via line 112. The aqueous phase comprised of tertiary butanol and water is removed from zone 108 via line 109 and passes to distillation column 110 for tertiary butanol recovery. In column 110 the mixture is fractionally distilled and a waste bottoms water stream is removed via line 111, part of which is recycled via lines 112 and 107 to phase separation zone to aid in tertiary butanol and ditertiary butyl peroxide separation therein and the remainder discarded.

A tertiary butanol and water azeotrope is taken overhead from column 110 via line 113 for further processing and recovery of the tertiary butanol.

An organic phase comprised of ditertiary butyl peroxide and tertiary butanol is removed from phase separator 108 via line 114 and passes to distillation column 115. A low boiling azeotrope of ditertiary butyl peroxide and tertiary butanol is removed from column 115 via line 116 and this stream is conveniently recycled to reactive distillation tower 102 for further tertiary butanol conversion.

Product ditertiary butyl peroxide essentially free of tertiary butanol (e.g. less than 1 wt %) and hydroperoxide (e.g. less than 0.1 wt %) is recovered via line 117.

The catalyst employed in packed catalyst bed 103 of tower 102 is preferably an acid catalyst such as zeolite H—Y or a solid sulfonic acid ion exchange resin such as XN1010.

Because the dehydration reaction which takes place in tower 102 is endothermic heat input means are suitably provided (not shown) in order to maintain the desired dehydration reaction temperature of 80°–150° C.

It is preferred in practice of the invention that dehydration temperature not exceed about 130° C. since at higher temperatures significant decomposition of ditertiary butyl peroxide takes place.

The following examples illustrate the invention:

EXAMPLE 1

In practice of the invention as set forth in FIG. 1, effluent from a reactor wherein debutanized isobutane oxidate comprised of tertiary butyl hydroperoxide and tertiary butyl alcohol is reacted with isobutylene to form ditertiary butyl peroxide is combined with an azeotropic ditertiary butyl peroxide and tertiary butyl alcohol stream and fed to dehydration zone 2 via line 1. Dehydration zone 2 contains three separate beds of zeolite H—Y supported by appropriate means with interstage reheat means provided; the number of separate dehydration stages can, of course, vary.

The feed to dehydration zone 2 is heated to 100°–130° C. and after passing through packed bed 3, the reaction mixture is reheated by means of heater 7 to dehydration temperature of 120° C. before passage through packed bed 4. Similarly, after passage through bed 4, the reaction mixture is reheated to 120° C. by means of heater 10 and then passed through packed bed 5.

In each of packed beds 3, 4 and 5, about 10–20% of the tertiary butanol in the feed is dehydrated to isobutylene, and tertiary butyl hydroperoxide and other peroxidic impurities are decomposed.

The reaction mixture from dehydration zone 2 is combined with recycle water and passes via line 11 to decantation zone 12. The aqueous phase passes via line 13 to distillation column 14 wherein an azeotropic tertiary butanol and water mixture is separated via line 18. The column 14 overhead temperature is 80° C. an overhead pressure is 5 psig.

Bottoms is removed via line 15 at 115° C. with a portion purged via line 17 and the remainder recycled via lines 16 and 11 to decantation zone 12.

An organic phase is removed from decantation zone 12 via line 19 and passes to distillation zone 20. An overhead isobutylene stream is removed at 50° C. and 60 psig via line 21 and is conveniently recycled to ditertiary butyl peroxide production (not shown).

A bottoms stream is removed at 120° C. and 60 psig from zone 20 via line 22 and passes to distillation zone 23. An overhead azeotrope of tertiary butanol and di-t-butyl peroxide is recovered overhead from zone 23 at 55° C. and 5 psia via line 24 and is recycled to dehydration zone 2.

The bottoms stream comprised of substantially pure di-t-butyl peroxide is separated from zone 23 at 100° C. and 5 psia via line 25 and represents the cetane grade product of the present process.

The amounts and compositions of the various streams are given in the following Table 1.

TABLE 1

| Component, lbs/hr. | Stream No. | | | | | |
|---|---|---|---|---|---|---|
| | 1 | 11 | 13 | 18 | 17 | 16 |
| Isobutylene | 15.1 | 33.2 | 0.0 | — | — | — |
| t-butyl hydroperoxide | 1.7 | 0.0 | 0.0 | — | — | — |
| t-butanol | 58.3 | 35.8 | 14.2 | 14.3 | 0.1 | — |
| Di-t-butyl peroxide | 70.5 | 70.5 | 0.7 | 0.7 | 0.0 | — |
| Lights | 8.0 | 8.2 | 3.3 | 3.3 | 0.0 | — |
| Heavie | 0.8 | 1.0 | 0.4 | 0.4 | 0.0 | — |
| Water | 4.3 | 42.6 | 40.4 | 2.0 | 6.0 | 32.4 |

| Component, lbs/hr. | Stream No. | | | | |
|---|---|---|---|---|---|
| | 19 | 21 | 22 | 24 | 25 |
| Isobutylene | 33.2 | 33.2 | 0.0 | — | — |
| t-butyl hydroperoxide | 0.0 | — | 0.0 | — | — |
| t-butanol | 21.5 | — | 21.5 | 21.5 | 0.0 |
| Di-t-butyl peroxide | 69.8 | — | 69.8 | 19.4 | 50.4 |
| Lights | 4.9 | — | 4.9 | 4.9 | 0.0 |
| Heavies | 0.6 | — | 0.6 | 0.0 | 0.6 |
| Water | 2.1 | — | 2.1 | 2.1 | 0.0 |

EXAMPLE 2

In practice of the invention as set forth in FIG. 2, effluent from a reactor wherein debutanized isobutane oxidate comprised of tertiary butyl hydroperoxide and tertiary butyl alcohol is reacted with isobutylene to form ditertiary butyl peroxide is combined with an azeotropic ditertiary butyl peroxide and tertiary butyl alcohol stream and fed to dehydration zone 102 via line 101. Dehydration zone 102 is a reactor distillation column provided with a central packed bed 103 of zeolite H—Y catalyst supported by conventional means. Fractional distillation zones 104 and 105 are located respectively above and below the catalyst bed.

The feed mixture is introduced via line 101 at an intermediate point at 100° C. and in reactive distillation column 101 tertiary butanol is dehydrated upon contact with the catalyst bed and any hydroperoxides are decomposed. Isobutylene product of dehydration is removed overhead via line 106 at 40° C. and 65 psig. This isobutylene is conveniently recycled to ditertiary butyl peroxide formation (not shown) with any excess recovered as product. Necessary heat is provided by reboiler means (not shown) to maintain conditions in 102.

Ditertiary butyl peroxide, water and some tertiary butanol pass downwardly through distillation zone 105 and are removed via line 107 at 120° C. and 70 psig and are passed to phase separation zone 108 together with additional water via line 112. The aqueous phase comprised primarily of tertiary butanol and water is removed from zone 108 via line 109 and passes to distillation column 110 for tertiary butanol recovery. In column 110 the mixture is fractionally distilled and a bottoms water stream at 115° C. removed via line 111, part of which is recycled via line 112 to phase separation zone 108 to aid in tertiary butanol and ditertiary butyl peroxide separation therein and the remainder discarded.

A tertiary butanol and water azeotrope is taken overhead from column 110 at 80° C. and 5 psig via line 113 for further processing and recovery of the tertiary butanol.

An organic phase comprised of ditertiary butyl peroxide and tertiary butanol is removed from phase separator 108 via line 114 and passes to distillation column 115. A low boiling azeotrope of ditertiary butyl peroxide and tertiary butanol is removed from column 115 via line 116 at 55° C. and 5 psia and this stream is recycled to reactive distillation tower 102 for further tertiary butanol conversion.

Product ditertiary butyl peroxide essentially free of tertiary butanol (e.g. less than 1 wt %) and hydroperoxide (e.g. less than 0.1 wt %) is recovered via line 117 at 100° C.

The amounts and compositions of the various streams are given in the following Table 2.

TABLE 2

| Component, lbs/hr. | Stream No. | | | | | |
|---|---|---|---|---|---|---|
| | 10 | 116 | 106 | 107 | 112 | 114 |
| Isobutylene | 15.1 | 0.0 | 37.9 | 0.0 | | 0.0 |
| t-butyl hydroperoxide | 1.7 | | | 0.0 | | 0.0 |
| t-butanol | 36.8 | 12.1 | | 20.1 | | 12.1 |
| Di-t-butyl peroxide | 51.1 | 10.8 | | 62.0 | | 61.4 |
| Lights | 3.1 | 4.9 | | 8.2 | | 4.9 |
| Heavies | 0.8 | 0.0 | | 1.0 | | 0.6 |
| Water | 2.2 | 1.2 | | 10.7 | 32.2 | 2.1 |

| Component, lbs/hr. | Stream No. | | | |
|---|---|---|---|---|
| | 109 | 117 | 113 | 111 |
| Isobutylene | 0.0 | | | — |
| t-butyl hydroperoxide | 0.0 | | | — |
| t-butanol | 8.0 | 0.0 | 8.0 | 0.0 |
| Di-t-butyl peroxide | 0.6 | 50.5 | 0.6 | 0.0 |
| Lights | 3.3 | 0.0 | 3.3 | 0.0 |
| Heavies | 0.4 | 0.6 | 0.4 | 0.0 |
| Water | 40.8 | 0.9 | 1.1 | 7.5 |

We claim:

1. The process for separating ditertiary butyl peroxide from admixtures with tertiary butanol which comprises contacting a mixture comprised of ditertiary butyl peroxide and tertiary butanol with a tertiary butanol dehydration catalyst at tertiary butanol dehydration conditions, converting at least a portion of the tertiary butanol to isobutylene and water, and separating ditertiary butyl peroxide having a reduced content of tertiary butanol from said isobutylene and water.

2. The process of claim 1 wherein the dehydration catalyst is an acidic zeolite.

3. The process of claim 1 wherein the dehydration catalyst is H—Y zeolite.

4. The process of claim 1 wherein the dehydration is carried out at 80°–150° C.

5. The process of claim 1 wherein the dehydration is carried out in a reactive distillation zone.

* * * * *